(12) United States Patent
Joseph et al.

(10) Patent No.: US 11,548,720 B2
(45) Date of Patent: Jan. 10, 2023

(54) HUMIDITY-STABLE PACKAGE OF DISPOSABLE ABSORBENT ARTICLES WITH WETNESS INDICATORS

(71) Applicant: The Procter & Gamble Company, Cincinnati, OH (US)

(72) Inventors: Laveeta Joseph, Cincinnati, OH (US); William Winfield Cheeseman, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 14/664,020

(22) Filed: Mar. 20, 2015

(65) Prior Publication Data

US 2015/0266663 A1    Sep. 24, 2015

Related U.S. Application Data

(60) Provisional application No. 61/955,973, filed on Mar. 20, 2014.

(51) Int. Cl.
*B65D 85/00* (2006.01)
*B65D 85/62* (2006.01)
(Continued)

(52) U.S. Cl.
CPC .............. *B65D 85/62* (2013.01); *A61F 13/42* (2013.01); *A61F 13/53* (2013.01);
(Continued)

(58) Field of Classification Search
CPC .... B65D 85/62; B65D 65/38; B65D 75/5827; B65D 85/16; B65D 75/5833; A61F 13/55115; A61F 13/42; A61F 13/53; A61F 2013/530481; A61F 2013/422; A61F 2013/428; A61F 13/84; A61F 13/5511; B29C 59/007; B29C 2791/009;
(Continued)

(56) References Cited

U.S. PATENT DOCUMENTS 3,790,744 A    2/1974  Bowen
3,812,002 A *  5/1974  Lurie ...................... B32B 15/08
                                                            156/155

(Continued)

FOREIGN PATENT DOCUMENTS

CN           2661614 Y      12/2004
CN         202244482 U       5/2012
(Continued)

OTHER PUBLICATIONS

Wayback Machine, Polypropylene from Wikipedia, Feb. 3, 2014.*
(Continued)

*Primary Examiner* — Anthony D Stashick
*Assistant Examiner* — James M Van Buskirk
(74) *Attorney, Agent, or Firm* — Amanda Herman Berghauer; William E. Gallagher

(57) ABSTRACT

A package comprising a plurality of disposable absorbent articles contained in an outer wrap is disclosed. The outer wrap is formed of a film having a thickness and has a path of scoring that partially but not completely penetrates the thickness, and defines a path of weakness in the film along which tear propagation is facilitated.

12 Claims, 7 Drawing Sheets

(51) Int. Cl.

| | |
|---|---|
| *A61F 13/551* | (2006.01) |
| *A61F 13/84* | (2006.01) |
| *B65D 75/58* | (2006.01) |
| *B65D 85/07* | (2017.01) |
| *A61F 13/42* | (2006.01) |
| *A61F 13/53* | (2006.01) |
| *B65D 65/38* | (2006.01) |
| *B29C 59/00* | (2006.01) |

(52) U.S. Cl.
CPC .... *A61F 13/5511* (2013.01); *A61F 13/55115* (2013.01); *A61F 13/84* (2013.01); *B65D 65/38* (2013.01); *B65D 75/5827* (2013.01); *B65D 75/5833* (2013.01); *B65D 85/07* (2018.01); *A61F 2013/422* (2013.01); *A61F 2013/424* (2013.01); *A61F 2013/428* (2013.01); *A61F 2013/530481* (2013.01); *B29C 59/007* (2013.01); *B29C 2791/009* (2013.01)

(58) Field of Classification Search
CPC .......... B32B 15/08; Y10T 428/31681; Y10T 428/31703; Y10T 428/31692; Y10T 428/2457; Y10T 428/24521; Y10T 428/24537; Y10T 428/15; Y10T 156/1041
USPC .......... 206/526; 428/43, 161, 163, 167, 458, 428/461, 464; 604/384; 493/395
See application file for complete search history.

(56) References Cited

U.S. PATENT DOCUMENTS

| | | | |
|---|---|---|---|
| 4,217,327 A | | 8/1980 | Cancio et al. |
| 4,551,191 A | | 11/1985 | Kock et al. |
| 5,328,053 A | | 7/1994 | Cook et al. |
| 5,342,861 A | | 8/1994 | Raykovitz |
| 5,783,266 A | * | 7/1998 | Gehrke .................. B32B 27/00 428/34.3 |
| 5,968,381 A | * | 10/1999 | Nusshor ................ B29C 59/007 219/121.69 |
| 6,124,391 A | | 9/2000 | Sun et al. |
| 6,307,119 B1 | | 10/2001 | Cammarota et al. |
| 6,359,049 B1 | | 3/2002 | Carrico et al. |
| 6,719,678 B1 | * | 4/2004 | Stern .................. B65D 33/2508 493/212 |
| 7,159,532 B2 | | 1/2007 | Klofta et al. |
| 7,303,092 B2 | | 12/2007 | Sarbo et al. |
| 7,520,873 B2 | | 4/2009 | Sosalla et al. |
| 8,585,666 B2 | * | 11/2013 | Weisman ................ A61F 13/53 604/368 |
| 8,618,349 B2 | | 12/2013 | Klofta |
| 8,632,518 B2 | | 1/2014 | LaVon et al. |
| 8,927,801 B2 | | 1/2015 | Klofta |
| 2003/0231811 A1 | * | 12/2003 | Hodson .................. B65D 31/02 383/208 |
| 2005/0103667 A1 | | 5/2005 | Fuchsberger |
| 2005/0276525 A1 | | 12/2005 | Hebert et al. |
| 2006/0124494 A1 | | 6/2006 | Clark, Jr. et al. |
| 2007/0020424 A1 | * | 1/2007 | Gruenbacher ........ A47L 23/266 428/40.1 |
| 2007/0284032 A1 | * | 12/2007 | Stoppelmann ........ B29C 59/007 156/272.8 |
| 2008/0058742 A1 | * | 3/2008 | Ales ........................ A61F 13/42 604/361 |
| 2009/0190866 A1 | * | 7/2009 | Hughes .................. B65D 75/44 383/207 |
| 2010/0026369 A1 | | 2/2010 | Hofmayer |
| 2010/0310198 A1 | | 12/2010 | Port et al. |
| 2011/0137274 A1 | * | 6/2011 | Klofta ..................... A61L 15/56 604/361 |
| 2012/0288660 A1 | * | 11/2012 | Maseiker .............. B29C 59/007 428/43 |
| 2012/0325176 A1 | | 12/2012 | Horn |
| 2012/0325716 A1 | | 12/2012 | Evenson et al. |
| 2013/0008824 A1 | | 1/2013 | Ito et al. |

FOREIGN PATENT DOCUMENTS

| | | |
|---|---|---|
| EP | 1 330 272 B1 | 6/2005 |
| EP | 1 242 027 B1 | 7/2007 |
| WO | WO 1991-16871 A1 | 11/1991 |

OTHER PUBLICATIONS

Wayback Machine, Polyethylene from Wikipedia, Feb. 3, 2014.*
PCT International Search Report dated Jul. 3, 2015 (11 pages).
Advantages of using Laser Technology vs. Mechanical, www.flexpakservices.com/why-lasers.htm, web page dated Sep. 30, 2010 (1 page).
Laser Perforating Equipment, www.lasx.com/laer-perforating-equipment.php, web page dated Sep. 30, 2010 (3 pages).
Lasers Assure the Flow and Flexibility of Aseptic Carton Production, Ela Fruscione, Converting Magazine, Aug. 1999 (1 page).
Microperforations for Fresh Cut Produce Packaging, Christopher Chow (6 pages).
Laser Processing—It's Part of the Package, Christopher Chow, Industrial Laser Solutions, Feb. 2002 (2 pages).
$CO_2$ Lasers for Flexible Food Packaging, William R. Dinauer and Frank Gaebler, www.laser-journal.de, 2008 (2 pages).
Improvements to Laser Processing of Thin Polymer Films—Using Non-Standard Novel Laser Wavelengths; Tony Hoult and Bill Dinauer (5 pages).
$CO_2$-Lasers Replace Mechanical Tooling, Euro Laser, Jun. 2008 (3 pages).
Laser Processing of Flexible Packaging Materials—An Open and Shut Case, David C. Henning, Flexible Packaging Magazine, Jun. 2002 (3 pages).

* cited by examiner

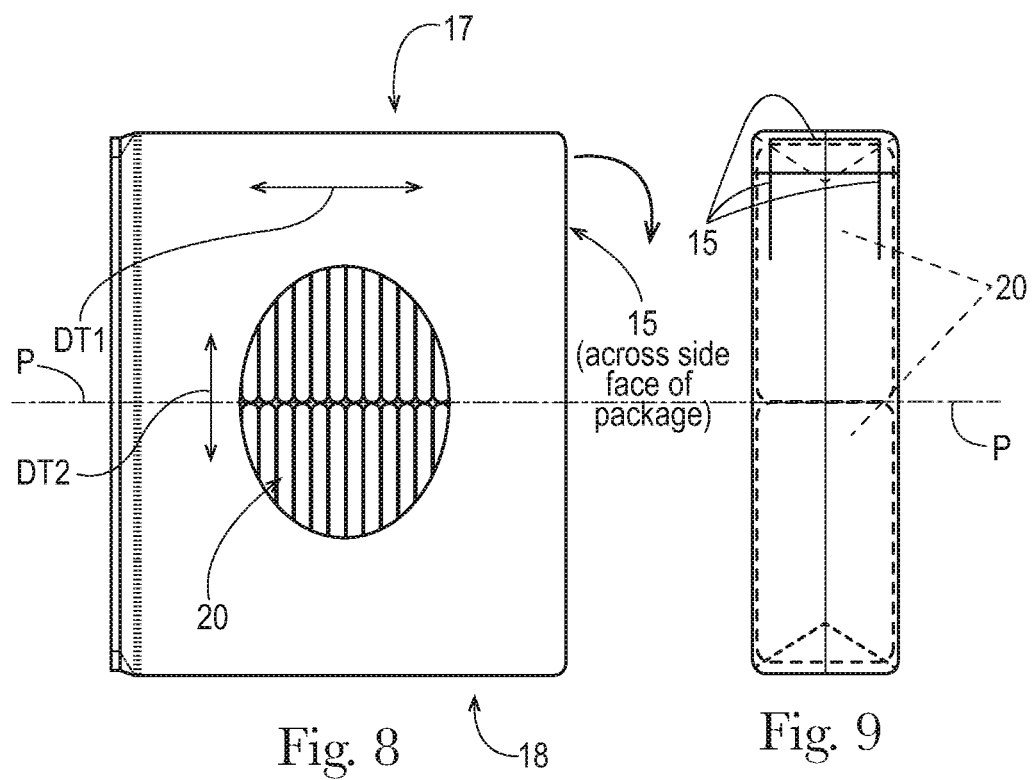

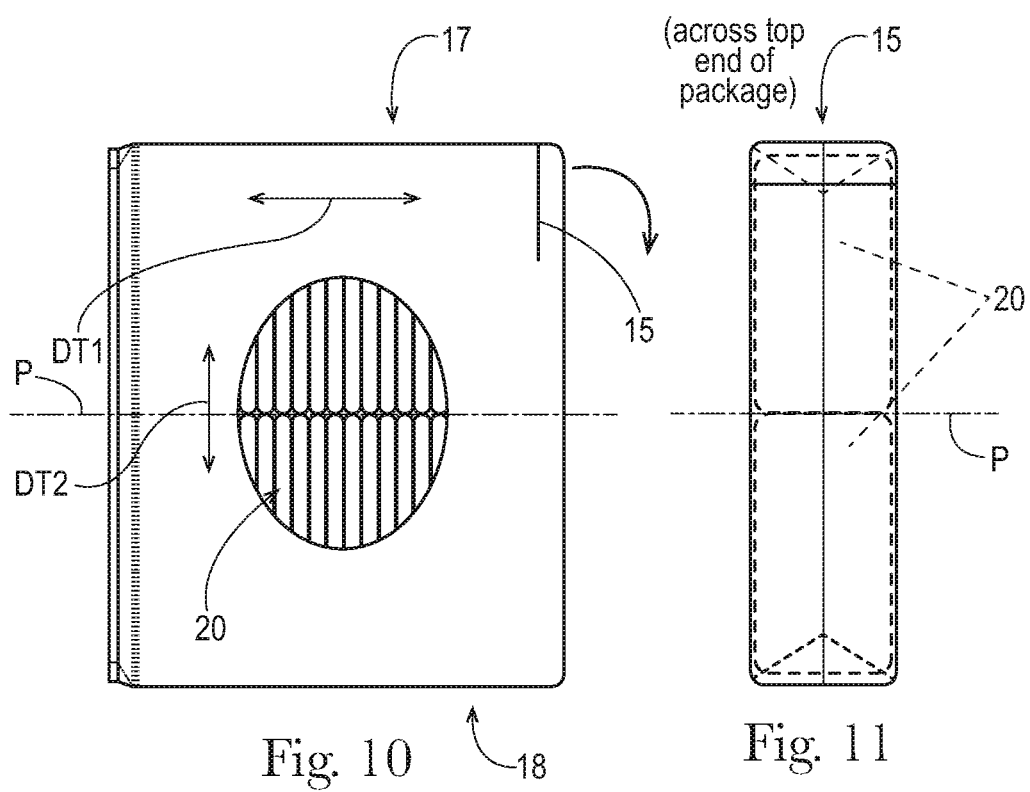

US 11,548,720 B2

HUMIDITY-STABLE PACKAGE OF DISPOSABLE ABSORBENT ARTICLES WITH WETNESS INDICATORS

CROSS REFERENCE TO RELATED APPLICATION

This applications claims the benefit of U.S. Provisional Application No. 61/955,973, filed Mar. 20, 2014, the substance of which is incorporated herein by reference.

BACKGROUND OF THE INVENTION

A number of manufacturers of disposable diapers offer variants having wetness indicators. A wetness indicator may include, for example, a chemically active device and/or material that provides a signal such as a visible change of appearance or other perceivable signal, noticeable to the caregiver, when the diaper is wetted. By provision of such a signal, the caregiver may be notified that the wearer has urinated in the diaper, which may indicate the need for a change. The need for the caregiver to manually check and feel the diaper with her hands for wetness may be thereby reduced or eliminated.

A number of manufacturers of disposable absorbent articles such as diapers and training pants, incontinence pants and feminine hygiene pads offer variants having absorbent cores that include particles of absorbent gelling materials, sometimes also known as superabsorbent polymers. Such particles attract and capture water molecules and are typically capable of absorbing many times their weight in water.

Disposable absorbent articles are often sold in stacks, in bags or packages formed of polymer film. The film is typically wrapped about one or more compressed stacks of articles and welded or adhered to itself along seams to form a closed bag or package. Because the film and the package must be sufficiently robust both to contain the one or more stacks of articles, often under compression, and to withstand shipping and handling, without breaking open, the package is, typically, also sufficiently robust as to be difficult for a consumer to open unless an opening aid is provided.

Currently opening aids are typically provided in the form of lines or other paths of perforations that have been die-cut through the film forming the package. A line or other path of perforations enables the consumer to initiate and propagate a tear therealong and create an opening into the package, through which articles may be withdrawn when needed.

Such perforations, however, compromise the film's ability to bar or inhibit entry of moisture into the package. In areas of relatively high temperature and humidity, entry of moisture through the perforations will be greater. When the articles in the package include wetness indicators, entry of moisture through the perforations may be sufficient to trigger the wetness indicators prior to use, and also may impart a damp feeling or otherwise degrade the supply of unused diapers in various ways. This may negatively affect the utility of the wetness indicator and the quality of the unused articles, and thus, may negatively affect consumer perception of the product.

Thus, an improvement in the way in which articles having wetness indicators as well as articles having materials that are prone to absorbing moisture from the air, are packaged, would give the manufacturer thereof a competitive advantage.

BRIEF DESCRIPTION OF THE DRAWINGS

FIG. 8 is a front view of another example of a package of disposable diapers.

FIG. 9 is a side view of the package of diapers shown in FIG. 8.

FIG. 10 is a front view of another example of a package of disposable diapers.

FIG. 11 is a side view of the package of diapers shown in FIG. 10.

DETAILED DESCRIPTION OF THE INVENTION

Figures 1, 2:
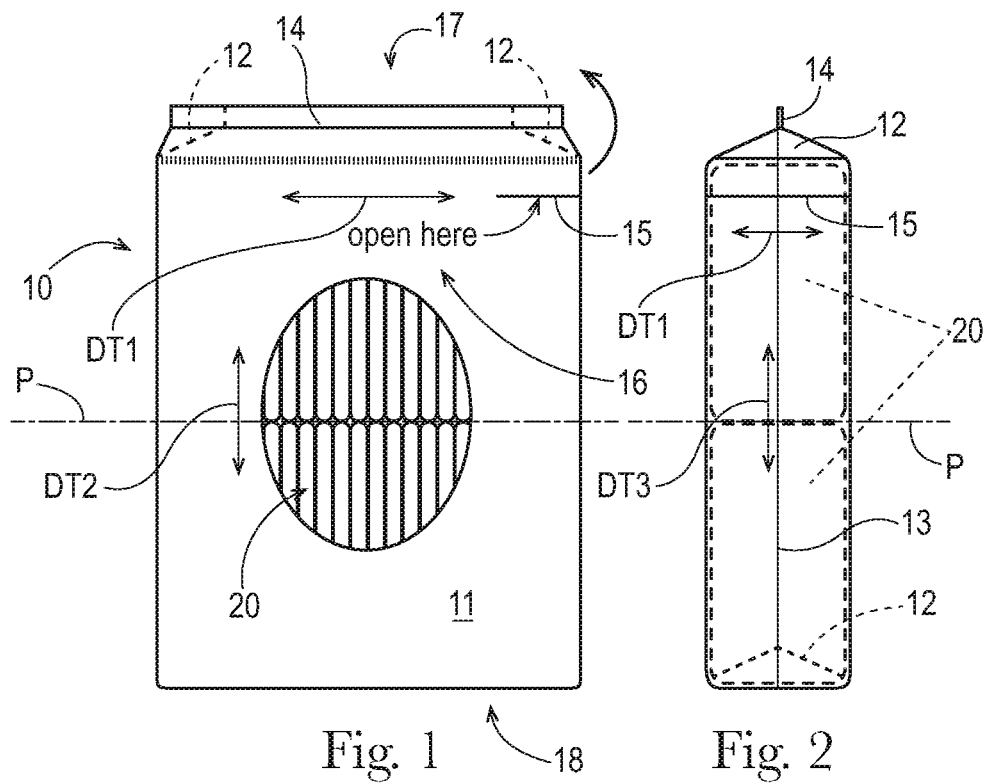
FIG. 1 is a front view of an example of a package of disposable diapers.
FIG. 2 is a side view of the package of diapers shown in FIG. 1.

For purposes herein, the following terms or phrases have the meanings set forth:

"Path of scoring" means a channel through and along one surface of a film, which may be continuous or discontinuous, formed by either the removal or displacement of material of the film previously occupying the space in the channel, and which does not fully penetrate the film in the z-direction.

"z-direction" means orthogonal to an x-y plane defined by a surface of a film or portion thereof when extended and laid out flat.

With respect to an absorbent article, "lateral" refers to the direction generally parallel to the waist edges, and "longitudinal" refers to the direction generally perpendicular to the waist edges.

Disposable absorbent articles such as disposable diapers, training pants, feminine hygiene pads and adult incontinence pants with absorbent cores including particles of superabsorbent polymer, have been known, and sold, for a number of years. See, e.g., U.S. Pat. No. 4,551,191. It has been recognized that articles containing particles of superabsorbent particles may be susceptible to degradation of various forms when stored in high-humidity environments, such as in the southern U.S. or in tropical regions. Various attempts to address this situation have been made. See, e.g., U.S. Pat. Nos. 8,632,518; 6,359,049; and 6,124,391. The described methods, however, have required adding materials and/or processing steps and costs to the manufacture of the articles.

Disposable absorbent articles such as disposable diapers having wetness indicators configured to change appearance when contacted by an effective amount of aqueous fluid (such as urine) also have been known, and sold, for a number of years. Examples are described in PCT App. Pub. No. WO 91/16871; U.S. Pat. Nos. 5,342,861 and 7,520,873; US Pat. App. Pub. No. US 2002/0007162; and European Pats. Nos. EP 1 242 027 B1 and EP 1 330 272 B1. It has been recognized that wetness sensors may be susceptible to being prematurely activated or rendered less effective in high humidity environments as a result of an attraction and uptake of airborne water molecules. Accordingly, more recently, attempts have been made to design wetness sensors that are relatively resistant to exposure to water vapor while remaining effective when contacted by aqueous liquid. See, for example, U.S. Pat. Nos. 7,159,532 and US Pat. App. Pub. Nos. US 2010/0262100; US 2010/0262099; US 2011/0137274 and US 2010/026369. Such designs, however, may in some circumstances be unacceptably expensive to manufacture and incorporate into disposable diapers, or may limit the color change rate or kinetics of the wetness indicator. This may impose a need to compromise one or the other of humidity resistance and quickness of color change upon being wetted.

To protect newly manufactured disposable absorbent articles from dirt, dust and moisture during shipping, handling and storage prior to sale, and for purposes of economy, the articles are typically packaged in compressed stacks contained in packages formed of polymer film. The packages may include one, two or more compressed stacks and contain a total of at least 20, 30, 40, 50, 60, 70, 80, 90 or more individual diapers. To withstand outward forces exerted against the walls of the package by the compressed stacks of articles, and varying forces and shocks experienced by the package during shipping and handling, without breaking open prior to sale, the films used to form such packages are typically selected to be sufficiently robust in that they possess suitable thickness, ductility and tensile strength. For purposes of economy, inexpensive polymers such as polyolefins may be preferred, for example, polyethylene. Polyethylene may be particularly preferred because it has a suitable combination of traditionally low resin cost, relatively low melting point (important for processing with relatively low energy costs) and ease of processability, and forms a film that has desirable ductility and tensile strength, and thus, tear resistance.

This tear resistance combined with suitable thickness for package integrity, however, provides a package that may be undesirably difficult for a consumer to open to access the diapers within. A frequently-employed solution to this problem has been to provide a path of perforations in the film, at which a consumer can forcibly initiate and propagate a tear in the film along the path of perforations to create an opening in the package.

Such perforations, however, entirely penetrate the package film and thus can permit water vapor to enter the package. In relatively high temperature, high-humidity environments (for example, subtropical and tropical geographic regions in which air conditioning for storage may not be present) moisture can enter a package in sufficient quantities to compromise the quality of the articles therein. It is believed that a typical period of time in which products of the kind may be stored between the time of delivery to the region and final retail sale may be up to 24 or even 36 months in some circumstances. During such a period of time in relatively high temperature and humidity, articles having absorbent cores including particles of superabsorbent polymers can absorb water from moist air entering through perforations, and take on a damp feel, agglomerate or clump, or discolor. Wetness indicators or sensors in articles in such conditions can absorb water from moist air in quantities sufficient to partially or completely trigger the indicators, rendering them partially or completely useless. Either or both of these conditions are generally undesirable to the consumer and can reflect poorly on the products.

Referring to FIGS. 1 and 2, a package 10 of absorbent articles 20 may have an outer wrap 11 formed of film. The outer wrap may be formed in a flow-wrap process, in which one or more stacks of absorbent articles 20 may be formed, compressed, and conveyed along with film stock to a flow-wrapping machine (not shown) which wraps the film about the stacks, forms tuck-folds 12 at the corners, welds the film along seams 13, 14, and may trim away excess film material. The one or more stacks of absorbent articles may be compressed along a direction, e.g., DT1. In the example depicted in FIG. 1, the articles 20 may be disposable diapers or pants, which after manufacture may be folded in half about their lateral axes and then stacked in the manner suggested in FIG. 1. The stacks may be compressed along the direction of stacking before or during packaging for purposes of volume economy in shipping and storage. When film material is used economically (i.e., the entire volume of the package is substantially filled along at least the dimension parallel the stacking direction), following packaging the film forming package 10 will be in tension at least along a direction parallel to the direction of stacking, e.g., in FIG. 1, direction DT1.

As an alternative to providing a path of perforations to provide a mechanism for opening the package, the manufacturer can provide a path of scoring 15 in the film. The scoring can penetrate the film to any suitable depth that is less than the film's z-direction thickness (i.e., the film is not entirely penetrated). It will be understood that the ease of initiation and propagating a neat tear in the material along path 15 to create an opening in the package 10 will in part depend upon the depth of the scoring relative the z-direction thickness t of the film. At the same time, if the scoring depth is too great relative the film thickness, the film at the location of the path of scoring may not have sufficient strength to withstand forces and shocks in shipping and handling without undergoing an unintended, premature rupture and tear along path 15 prior to retail sale. Thus, in selecting scoring depth, it may be desired to find an appropriate balance between ease of tearing and package robustness, depending on the composition and thickness of the film material or different layers thereof.

One method of creating a path of scoring may include use of a die that is sufficiently controlled in the scoring process so as to penetrate the film only to the desired depth. A die may have a u-shaped or v-shaped cross-sectional profile configured to plastically deform, separate and/or displace material of the film when impressed thereon. In one example, the die may be heated so as to facilitate plastic deformation and displacement of material to create the scoring channel.

Figure 13A:
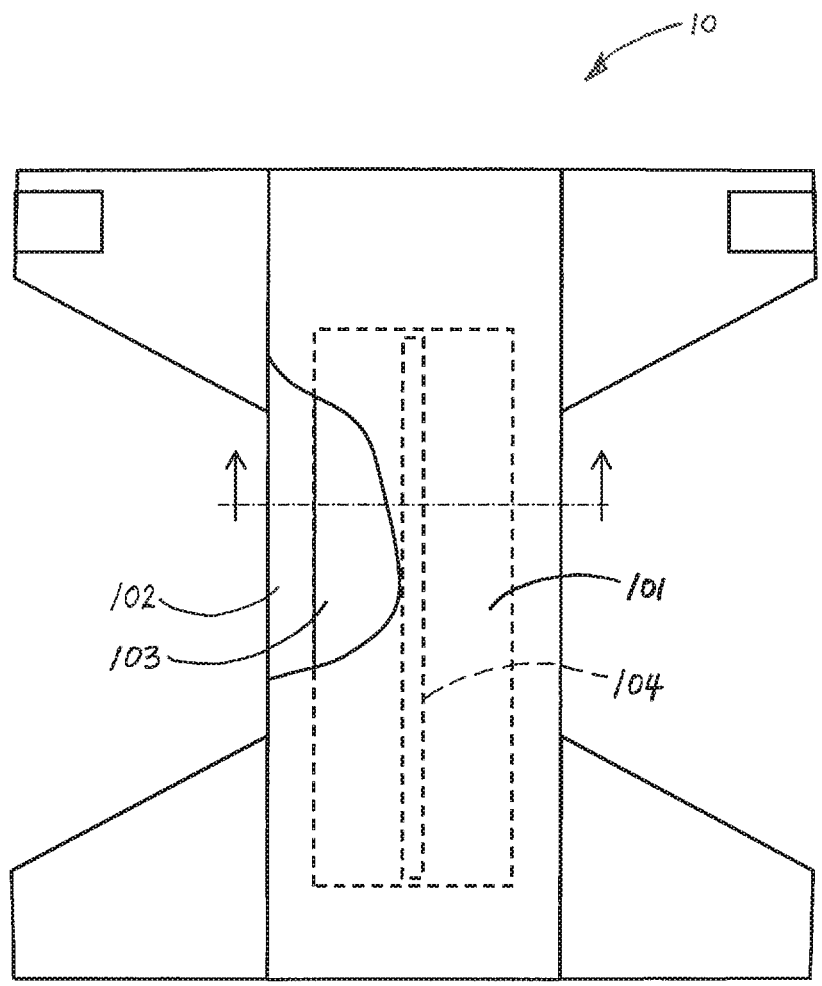
FIG. 13A is a schematic plan view of a disposable diaper.
Figure 13B:
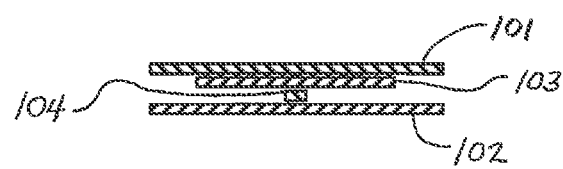
FIG. 13B is a schematic cross section of the diaper depicted in FIG. 13A, taken along lines 13B-13B in FIG. 13A.

Referring to FIGS. 13A and 13B, a disposable absorbent article such as a disposable diaper 10 may include a liquid permeable topsheet 101, a liquid impermeable backsheet 102 and an absorbent core 103 disposed between the topsheet and the backsheet. The absorbent core may include therewithin particles of absorbent gelling materials, sometimes also known as superabsorbent polymers (not specifically shown). A disposable diaper 10 may also include a wetness indicator 104.

Another method of creating a path of scoring may include use of a beam of laser light that is suitably powered, tuned, controlled and guided so as to displace or remove material (burning, vaporizing or melting, or a combination thereof) along the desired path in the film stock, prior to flow-wrapping. Laser scoring of film has been used in the food packaging industry, and appropriate laser light generating and guiding equipment is available. Suitable laser scoring and control equipment is available, for example, from LasX Industries, Inc., St. Paul, Minn.

The laser beam's wavelength and power may be selected and adjusted to penetrate the material of the film to a desired depth. Under certain circumstances, a laser may be selected and/or adjusted to score through one type of material without substantially scoring through another. Accordingly, in one example a film having two or more layers may be selected to form package 10, and a laser light source may be selected and/or adjusted so as to score through one of the layers but not the other(s) to any substantial extent. Suitable laser scoring equipment is available, for example, from LasX Industries, Inc., St. Paul, Minn.

Figure 4:
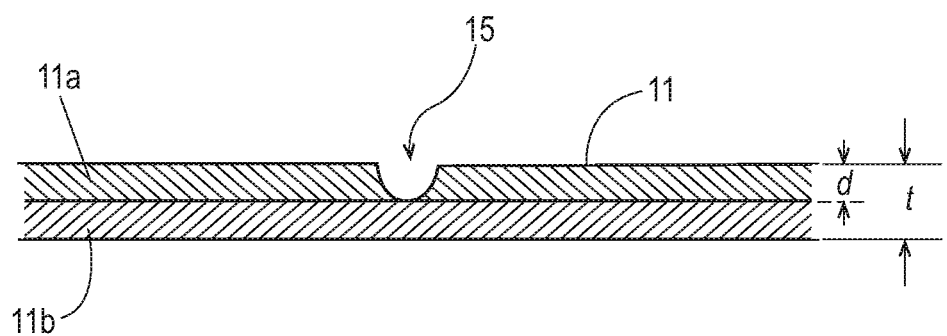
FIG. 4 is a schematic cross section of a portion of film bearing a path of scoring.
Figure 5:
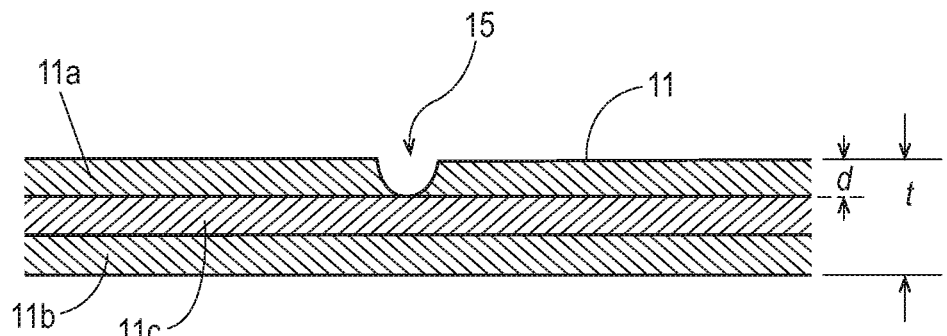
FIG. 5 is a schematic cross section of a portion of film bearing a path of scoring.

Referring to FIGS. 4 and 5, a multi-layer film 11 may be selected for use to form a package 10 with a path of laser scoring. The multi-layer film 11 may have, for example, an outer layer 11a formed of a first polymer (or first polymer blend) and an inner layer 11b formed of a second polymer (or second polymer blend). In another alternative, the multi-layer film may have an outer layer 11a formed of a first polymer (or first polymer blend), one or more intermediate layers 11c formed of a second polymer (or second polymer blend), and inner layer 11b formed of the first polymer (or blend) or a third polymer (or their polymer blend). (As used herein, the terms "outer layer" and "inner layer" refer to the positioning of the layer relative the interior and the exterior of the finished package; thus, the "inner layer" faces the contained product, and the "outer layer" faces outward and is visible to the consumer.) If flow-wrapping machinery is used to form any of seams 13 that join the film stock to itself by applying heat that causes the film to weld or fuse to itself, it may be desirable that the inner layer be formed of a polymer (or blend) that has a lower melting temperature than the polymer(s) (or polymer blend(s)) used to form the outer layer and/or intermediate layer(s). This enables heat energy to be applied to heat the inner layer to a degree sufficient to cause it to weld or fuse to itself, but not sufficient to cause undesired or excessive melting and deformation of the other layers. The outer, inner and any intermediate layers may be co-formed (such as by coextrusion), or in another example, may be separately formed and then laminated together following their formation, by use of one or more suitable laminating adhesives. In this latter example, an advantage provided is that one of the layers may be printed on one side before lamination. Following that, the printed side may be faced toward the other layer(s)) during lamination, such that it is covered and protected by the other layer(s) from abrasion and wear in the finished film product, thereby preserving the integrity of the printed images, graphics, verbal content, etc. When the other layer(s) are formed of substantially translucent or transparent materials, the printing may be seen therethrough.

The film composition and construction may be selected according to manufacturing, processing and packaging needs. For example, a multi-layer film may be desired for purposes of providing protection for printed package artwork as well as amenability to laser scoring. Polyethylene may be preferred for its relatively low cost, relatively low melt temperature and amenability to processing, and may be particularly desired for use in forming an inner layer or a substantial component thereof. A polyethylene material having a differing formulation and higher melt temperature may be selected to form an intermediate and/or outer layer or substantial components thereof. In another alternative, a polypropylene may be selected as a component for these intermediate and/or outer layers, or a blend of several polymers differing from that of the inner layer. In still yet other alternatives, other materials may be selected to form all or portions of the intermediate and/or outer layers, including but not limited to polylactic acid (PLA), which may provide the benefit of reducing use of materials derived from petroleum.

A suitable multilayer film 11 may be formed of one or more polyolefins, such as polypropylene or a blend of resins containing a predominate weight percentage of polypropylene; and polyethylene or a blend of resins containing a predominant weight percentage of polyethylene. As noted, the inner layer 11b may be formed of polyethylene or a blend of resins including polyethylene at a weight content greater than 50%. In a non-limiting example, a layer formed predominately of polypropylene having a first relatively higher melting temperature, and a layer formed of predominately of polyethylene having a second relatively lower melting temperature, may be used to form the outer and/or intermediate, and inner layers, respectively. In another non-limiting example, a multilayer film may include an inner layer of LLDPE (linear low density polyethylene), and a second layer of a blend or alloy of polyethylene variants of low density, medium density and high density. Optionally, a third layer may include a blend of LLDPE and LDPE (low density polyethylene).

Referring to FIGS. 1-5, an outer layer 11a may be scored by a die or by laser light to form a path of scoring 15, forming a path in the film along which tear initiation and propagation is facilitated and guided. A die may be suitably configured and controlled so as not to cut, perforate or penetrate the film in the z-direction to an extent beyond the desired scoring depth. A laser light source may be selected and adjusted so as to score through the polymer of an outer layer 11a without substantially penetrating the entire layer (e.g., FIG. 3), or penetrating intermediate layer(s) 11c and/or inner layer 11b (FIGS. 4, 5). This leaves a portion of the film such as the intermediate layer(s) 11c and/or inner layer 11b at least partially intact so as to provide a moisture barrier that inhibits the passage of water vapor at the path of scoring into the package. Accordingly, the material of an intermediate and/or inner layer may be selected so as to have a water vapor transmission rate insufficient to allow moisture to enter the package at the scored area to an undesirable extent.

For reasons in addition to effects on moisture barrier capabilities, the thickness of a combination of an inner layer 11b with any intermediate layer(s) 11c might be selected and/or controlled so that it is not so thin as to permit unintended rupture or tearing thereof during shipping and handling of the package, prior to intentional opening by the consumer after purchase. In many current processes for manufacturing and handling flow-wrap packages of the nature of absorbent articles packages, the packages may be dropped and shifted by equipment in various and random orientations before being packaged in larger protective containers for shipping. The film layer(s) underlying the path of scoring should be sufficiently strong so as not to permit unintended premature tearing during such handling.

At the same time, the path of scoring 15 should be deep enough into the film to enable the consumer to tear the film along the path to create an opening in the package without an unacceptable degree of effort. It is believed that consumers will find tearing of the film to be acceptably easy when the tensile strength of the scored film, measured along a direction perpendicular to the path of scoring 15, to be no more than about 15 Newtons/cm (per cm width of a specimen of the sample tested—measured along a direction parallel with the path of scoring), more preferably no more than about 11 N/cm, or 9.0 N/cm, or even no more than about 7.0 N/cm, where tensile strength is measured according to the Scored Film Tensile Test Method described herein. It will be appreciated that the extent to which such directional tensile strength across a path of scoring is sufficient for maintaining package integrity during handling prior to sale to the consumer will depend upon the magnitudes and orientations of tensile forces the package film must sustain prior to sale, resulting from, e.g., compression of the contents and/or pressure exerted on the package film by the contents, weight of the package, extent and levels of shocks the package is likely to undergo during pre-sale handling, and orientation of the path of scoring relative the greatest tensile forces the package film will undergo. As will be noted below, package integrity may be best protected when a straight path of scoring on a package face is closer to parallel the direction of greatest tensile force in the film on that face, than not.

The depth of scoring through the film material needed to achieve the desired consumer-acceptable ease of tearing (reflected in tensile strength across the path of scoring, as explained above) will vary according the thickness(es) and composition(s) of the film layer(s). In this regard, it may be desired that the layer(s) beneath the path of scoring (the layer(s) that remain substantially unscored) have a tensile strength along a direction perpendicular to the path of scoring that lies within the limits set forth above—because the path of scoring through the outer layer reduces the tensile strength of the scored layer in the direction perpendicular to the scoring. Accordingly, it may be desired that the layer(s) beneath the outer layer have a tensile strength that is no more than about 15 Newtons/cm (per cm width of a specimen of the sample tested—measured along a direction parallel with the path of scoring), more preferably no more than about 11 N/cm, or 9.0 N/cm, or even no more than about 7.0 N/cm, where tensile strength is measured according to the Scored Film Tensile Test Method described herein.

Figure 3:
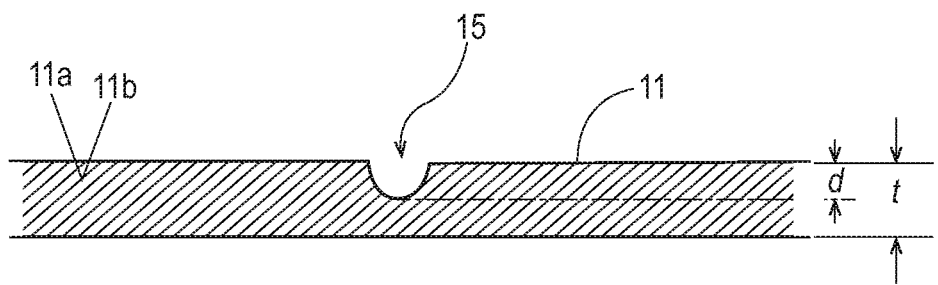
FIG. 3 is a schematic cross section of a portion of film bearing a path of scoring.

Further, it may be important that the path of scoring in the film be sufficiently deep so as to be effective at facilitating orderly propagation of a tear along the path of scoring, i.e., a tear that does not tend to easily stray away from the path of scoring. Without intending to be bound by theory, it is believed, accordingly, that the depth of the scoring (measured from the outside surface of the film) should be no less than 10%, more preferably no less than 12%, and still more preferably no less than 14% and even more preferably no less than 16% of the overall thickness t of the film, for films of any of the types contemplated herein. With reference to FIGS. 3-5, this percentage reflects calculation of depth d of path of scoring 15, divided by film thickness t, ×100%. Scoring depth is to be measured using the Scoring Depth Measurement Method described below.

The shape and orientation of path of scoring 15 may be deemed important. Preferably, the path of scoring will be straight. Alternatively, it may be preferable that the path include few or no sharp turns or corners, which can have the effect of localizing stresses that can promote tear propagation that strays beyond or outside of the path of scoring 15. Thus, it may be preferred that the path of scoring 15 does not include any curve having a radius less than 10 mm along any portion of the path length more than 1.0 cm from an end thereof.

Figure 6:
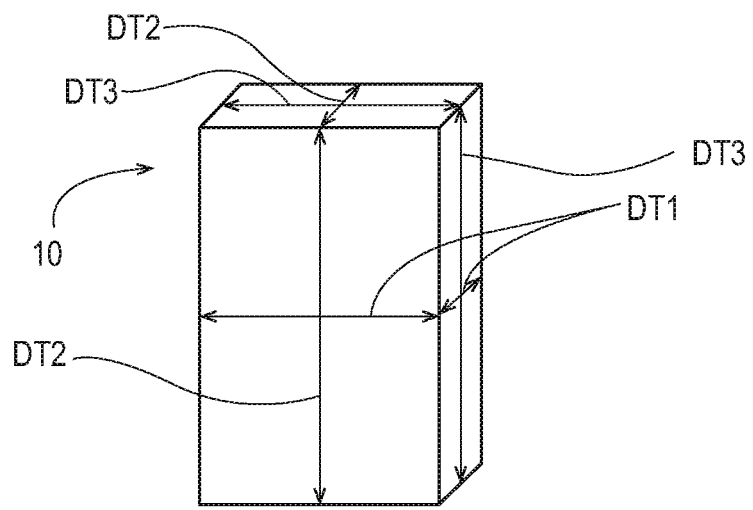
FIG. 6 is a schematic perspective view of a package showing directions of tension in the film of the faces thereof.

Referring to FIG. 6, as a result of an approximately rectangular cuboid shape of a stack of folded articles, a package of the type contemplated herein may have an approximately rectangular cuboid form, with six faces consisting of pairs of oppositely-disposed approximately rectangular sides formed of the package film. As a result of compression of the stack(s) of articles within the package, the film of each face may be under tension along two of three primary directions DT1, DT2 and DT3 which are, respectively, perpendicular and parallel to the side edges of the face. Unequal compressive forces restraining the contained articles in the package along the two primary directions can cause the highest tensile force in the film along one of these directions to be greater than that the highest tensile force in the film along the other direction. For example, referring to FIG. 1, if articles are stacked and packed within the package under relatively heavy compression along direction DT1, and relatively light compression along direction DT2, the highest tensile forces in the package film along direction DT1 on the faces shown in FIGS. 1 and 2 may be greater than those along directions DT2 and DT3.

To maximize package structural integrity when the package bears a path of scoring, it may be desired that less than 20 percent, more preferably less than 15 percent, and still more preferably less than 10 percent, of the total length of the path of scoring 15 on a face, be perpendicular to the direction of the greatest tensile force in the film of that face along one of directions DT1, DT2 or DT3. This reduces chances that stresses in the package film 11 resulting from restraining the compressed stack(s) of articles from expanding will promote an unintended, premature rupture along the path of scoring 15. (The "total length" of a path of scoring on a face is its continuous/uninterrupted length along the face, not necessarily linear.) In accordance with the above, as suggested in FIGS. 1 and 2, it may be desired that each of the respective portions of path of scoring 15 disposed on any face be substantially straight, and lying along a line forming an angle with the direction of the greatest tensile force on the face along direction DT1, DT2 or DT3 that is less than 45°, more preferably less than 30°, still more preferably less than 10°, and most preferably substantially 0°, i.e., substantially parallel with the direction of greatest tensile force along direction DT1, DT2 or DT3 on the face (as depicted, e.g., in FIGS. 1 and 2).

In conjunction, or separately, as suggested in FIGS. 1, 2 and 8-11, the path of scoring 15 may be configured and located such that the majority of its length lies near an end of the package so as to facilitate creation of an access opening nearer the end by tearing, as indicated by the large arrow in the Figures. This leaves a large portion of the package intact so that it may be used to continue to contain and store the supply of unused articles after opening of the package, and may also in some circumstances serve to dispose the path of scoring at locations of the package film likely to be under relatively lower tension. For example, the path of scoring 15 may be disposed at locations on one or more faces such that the majority of its path length (on all faces, cumulatively) lies closer to an end of the package than to its middle—as depicted by way of example in Figs. FIGS. 1, 2 and 8-11. (For purposes of the description in this paragraph, the "ends" of a package are the oppositely-disposed faces of the package with inside surfaces that abut or face waist edges or lateral folds of the articles in the stack(s) contained in the package, situated approximately in planes that are parallel to the direction of stacking of the individual articles; and the "middle" is the imaginary plane between the "end" planes, parallel to and equidistant from them. For example, in FIGS. 1, 2 and 8-11, the "ends" are the top and bottom faces 17, 18 of the package 10 relative the orientation shown in the figures because they abut or face waist edges of, or lateral folds in, the articles 20 in the contained stacks. The direction of stacking of individual articles 20 is parallel to DT1 in FIGS. 1, 8 and 10. The "middle" is the imaginary plane P shown passing through FIGS. 1, 2 and 8-11.)

Referring to FIG. 1, because a path of scoring as described herein may be less inherently visible than a path of perforations in the package film, it may be desired to include an indicium 16 proximate the path of scoring 15. Such an indicium 16 may be simply a printed instruction or any other indication that is effective to visually and/or verbally identify the location of the path of scoring on the package. Such an indicium may be printed on the inner surface of outer layer 11 a as described above for other printed graphics, images and information, or may be printed on the outer surface of film 11.

Scored Film Tensile Test Method

The tensile strength of a specimen of scored film is measured on a constant rate of extension tensile tester with computer interface (a suitable instrument is the MTS Alliance using Testworks 4.0 Software, as available from MTS Systems Corp., Eden Prairie, Minn.) using a load cell for which the forces measured are within 10% to 90% of the limit of the cell. Both the movable (upper) and stationary (lower) pneumatic jaws are fitted with rubber faced grips, wider than the width of the test specimen. All testing is performed in a conditioned room maintained at about 23° C.±2° C. and about 50%±2% relative humidity.

Figure 7:
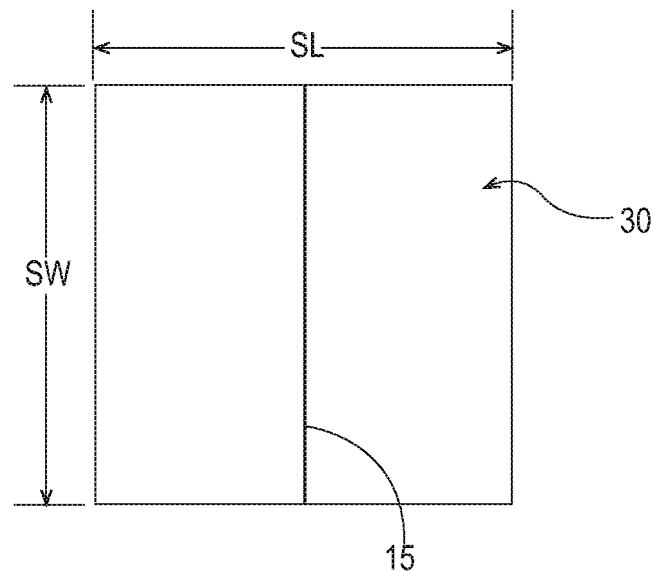
FIG. 7 is a plan view of a specimen of film having a path of scoring.

To prepare a specimen from a sample package with a path of scoring, cut the package film about the perimeter of the package at a location suitably removed from the path of scoring and from the location where the specimen will be taken as described below, so as to create a large opening that enables easy emptying of the package contents, and empty the package. Lay the remaining portion of the package on a work table so that the film proximate the path of scoring 15 is laid flat, and using a sharp Exacto knife or sharp scissors, cut a rectangular specimen 30 therefrom that is 5.08 cm (±0.05 cm) (specimen length SL) by 5.08 cm (±0.05 cm) (specimen width SW), with the path of scoring 15 perpendicular to and equally dividing the specimen length SL as shown in FIG. 7. Avoid including any seams in the specimen. Condition the specimen inside the conditioned room for at least 24 hours prior to testing.

For analysis, set the gage length to 25.4 mm. Zero the crosshead and load cell. Insert one of the specimen ends approximately 12.7 mm into the upper grips, aligning the length SL vertically within the upper and lower jaws (with path of scoring 15 perpendicular the direction of pull and centered between the gap between the upper and lower grips) and close the upper grips. Insert the other of the specimen ends approximately 12.7 mm into the lower grips and close the lower grips. After clamping in both grips the specimen should be under enough tension to eliminate any slack, but less than 0.05 N of force on the load cell.

Program the tensile tester to perform an extension test, collecting force and extension data at an acquisition rate of 50 Hz as the crosshead raises at a rate of 100 mm/min until the specimen breaks apart. Start the tensile tester and data collection. Program the software to record Peak Force (N) from the constructed force (N) verses extension (mm) curve. Calculate tensile strength as:

Tensile strength=Peak Force (N)/width of specimen (cm)

Analyze all specimens in substantially identical manner. Record tensile strength to the nearest 0.01 N/cm. A total of 10 specimens, taken one each from 10 sample packages, are analyzed. Calculate and report the average and standard deviation of tensile strength to the nearest 0.01 N/cm for the ten specimens.

Scoring Depth Measurement Method

The depth of a path of scoring is measured using a GFM MikroCAD Light instrument commercially available from GFMesstechnik GmbH, Teltow/Berlin, Germany. The GFM MikroCAD Light instrument consists of the following main components: a) DLP projector with direct digital controlled micro-mirrors; b) CCD camera with at least a 1600×1200 pixel resolution; c) projection optics adapted to a measuring area of at least 5×4 mm; d) recording optics adapted to a measuring area of at least 5×4 mm; e) a table tripod based on a small hard stone plate; f) a blue LED light source; g) a measuring, control, and evaluation computer running ODSCAD software (version 6.2, or equivalent); and h) calibration plates for lateral (x-y) and vertical (z) calibration available from the vendor.

The GFM MikroCAD Light system measures the surface height of a sample using the digital micro-mirror pattern fringe projection technique. The result of the analysis is a map of surface height (z axis) versus displacement in the x-y plane. The system has a field of view of 5×4 mm with an x-y pixel resolution of approximately 3 microns. The height resolution is set at 0.1 micron/count, with a height range of ±1.0 mm. All testing is performed in a conditioned room maintained at about 23±2° C. and about 50±2% relative humidity.

Calibrate the instrument according to manufacturer's specifications using the calibration plates for lateral (x-y) and vertical (z) available from the vendor.

To prepare a specimen from a sample package with a path of scoring, cut the package film about the perimeter of the package, at a location suitably removed from the path of scoring, to create a large opening that enables easy emptying of the package contents, and empty the package. Lay the remaining portion of the package on a work table so that the film proximate the path of scoring is laid flat, and cut out a square specimen that is 5.08 cm (±0.05 cm) (specimen length SL) by 5.08 cm (±0.05 cm) (specimen width SW), with the path of scoring 15 perpendicular to and equally dividing the specimen length SL as shown in FIG. 7. Avoid including any seams or creases in the specimen. Condition the specimen inside the conditioned room for at least 24 hours prior to testing.

Center the specimen within the camera field of view with respect to both the specimen length and width, so that a middle 5 mm portion of the length of the scoring path on the specimen is visible in the field of view, and approximately equal portions of unscored film appear on either side of the scoring path. The specimen should lay flat on the table. Place a glass slide on the film surface to keep it flat.

Collect a height image of the specimen by following the instrument manufacturer's recommended measurement procedures. Select the Technical Surface/Standard measurement program with the following operating parameters: (a) utilization of fast picture recording with a 3 frame delay; (b) a single level Phaseshift defined as a 16 pixel stripe width with a picture count of 12, and (c) a full Graycode starting with pixel 2 and ending with pixel 1024. After selection of the measurement program, continue to follow the instrument manufacturer's recommended procedures for focusing the measurement system and performing the brightness adjustment. Perform the 3D measurement then save the height image and camera image files.

Load the height image into the analysis portion of the software via the clipboard. Apply a polynomial filter of the material part with a rank of n=5, and select the difference image for height analysis.

Scoring Depth

Figure 12:
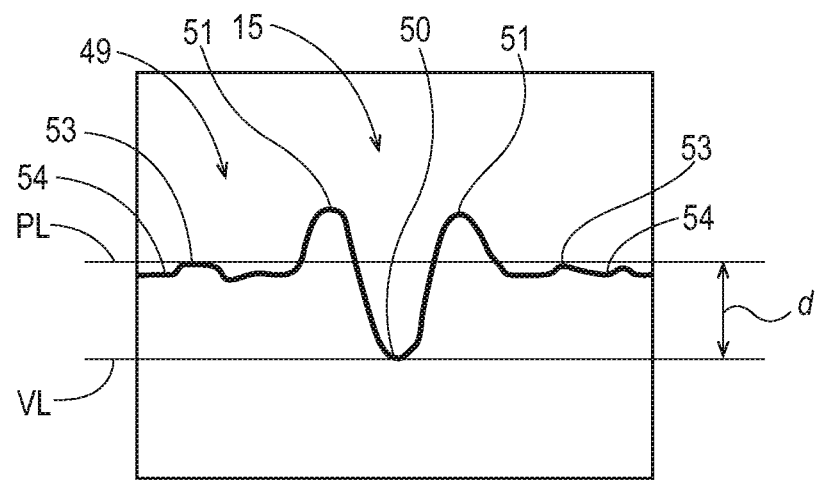
FIG. 12 is a schematic depiction of a sectional image of the height image created according to the Scoring Depth Measurement Method described herein.

On the filtered height image draw a line across, perpendicular to and equally dividing the length of the scoring path appearing in the image, extending beyond the scoring path onto the film surface on either side of the scoring path. Generate a sectional image of the height image along the drawn line. The sectional image will have an appearance with similarities to that shown in FIG. 12, depicting a cross-section of the film surface 49 scored by scoring path 15 with valley 50. When scoring path 15 has been created, for example, by laser, major peaks 51 of displaced film material may appear on either side of scored valley 50. Under the magnification of the film cross section reflected in the sectional image, the unscored/undisturbed film surface 49 outside the scoring path 15 and major peaks 51 may not be perfectly flat, but rather, may show irregularities with minor peaks 53 and minor depressions 54 thereon. Measure the surface-to-valley depth d as the vertical distance between two horizontal reference lines PL and VL selected to be tangent to the top of the highest of the minor peaks 53 and to the bottom of the scored valley 50, respectively, as shown in FIG. 12.

A total of 10 specimens, taken one each from 10 sample packages, are analyzed. Analyze all replicate specimens in a substantially identical manner. Record the height to the nearest 0.1 μm. Calculate and report the average and standard deviation of depth of scoring measures to the nearest 0.1 μm for the ten specimens.

Film Thickness

Thickness of a package film is measured using a ProGauge Thickness Tester (Thwing Albert, Glen Ellyn, Ill. USA) with a foot diameter of 2 inches at a pressure of 0.2 psi. Empty the package of its contents and cut out a 4 inch square film specimen from a location devoid of any creases, seams, perforations or scoring. The specimen is placed flat on the anvil with the test site centered underneath the caliper foot. The foot is lowered at 5.08 mm/sec. to an applied pressure of 0.2 psi. The reading is taken after 5 sec., and the foot is raised. A total of 10 specimens, taken one each from 10 sample packages, are analyzed. Analyze all replicate specimens in a substantially identical manner. Record the thickness to the nearest 1 μm. Calculate and report the average and standard deviation of the thickness to the nearest 1 μm for the ten specimens. All testing is performed in a conditioned room maintained at about 23±2° C. and about 50±2% relative humidity. Condition the specimen inside the conditioned room for at least 24 hours prior to testing.

Percent Depth of Scoring

The percentage depth of scoring is calculated by dividing the average depth of scoring by the average film thickness and multiplying by 100. Report the percent depth of scoring to the nearest 1%.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description are, in relevant part, incorporated herein by reference; the citation of any document is not to be construed as an admission that it is prior art with respect to the claims. To the extent that any meaning or definition of a term in this document conflicts with any meaning or definition of the same term in a document incorporated by reference, the meaning or definition assigned to that term in this document shall govern.

While particular embodiments have been illustrated and described, it would be obvious to those skilled in the art that various other changes and modifications can be made without departing from the spirit and scope of the invention. It is therefore intended to cover in the appended claims all such changes and modifications that are within the spirit and scope of this invention.

What is claimed is:

1. A package, said package having three primary directions DT1, DT2 and DT3 comprising:
    one or more stacks comprising a plurality of disposable diapers or absorbent pants, each of the plurality of disposable diapers or pants comprising a liquid permeable topsheet, a liquid impermeable backsheet, an absorbent core comprising particles of super absorbent polymer, disposed between the topsheet and the backsheet, and a wetness indicator adapted to change in appearance from a first appearance to a second appearance when activated by an effective amount of an aqueous fluid;
    said one or more stacks being compressed along a direction of stacking;
    an outer wrap containing the plurality of disposable absorbent articles, the outer wrap being formed of a multi-layer film having a thickness and comprising a first layer formed of polymer resin and a second layer formed predominantly of polyethylene and disposed adjacent the first layer, the multi-layer film having a path of scoring that partially but not completely penetrates the thickness of the multi-layer film and defines a path of weakness in the film along which tear propagation is facilitated, wherein the scoring has been created via laser;
    wherein the first layer defines an outer layer of the package;
    wherein the partial scoring extends through the first layer but not into the second layer; and
    said package having a rectangular cuboid form, with six faces consisting of oppositely-disposed approximately rectangular sides formed of said multi-layer film; said film of each face being under tension as a result of said compression of said one or more stacks along two of three primary directions DT1, DT2 and DT3, which are, respectively, perpendicular and parallel to the edges of the face; and
    wherein, less than 20 percent of the total length of the path of scoring on a face is perpendicular to the direction of the greatest tensile force in the film of that face along one of directions DT1, DT2, or DT3, whereby premature rupturing along said path of scoring due to stresses on the package film resulting from restraining the compressed one or more stacks of articles from expanding will not occur.

2. The package of claim 1, wherein the polymer resin comprises polyethylene.

3. The package of claim 1, wherein the multilayer film further comprises one or more intermediate layers disposed between the first layer and the second layer.

4. The package of claim 1, wherein the package comprises printed artwork.

5. The package of claim 1, wherein the path of scoring lies along a line forming an angle with the direction of the greatest tensile force on the face along direction DT1, DT2 or DT3 that is less than 45°.

6. The package of claim 1, wherein the outer layer comprises an indicium proximate the path of scoring.

7. The package of claim 1, wherein the path of scoring is substantially straight.

8. The package of claim 1, wherein the path of scoring does not comprise a curve having a radius less than 10 mm along any portion of the path length.

9. The package of claim 1, wherein the package comprises two stacks comprising a plurality of disposable diapers or absorbent pants.

10. The package of claim 8, wherein the plurality of disposable diapers or absorbent pants are folded in half about their lateral axes.

11. The package of claim 1, wherein the scoring has a depth no less than 10% of the overall thickness of the multi-layer film.

12. The package of claim 1, wherein the scoring has a depth no less than 16% of the overall thickness of the multi-layer film.

* * * * *